US006880211B2

(12) United States Patent
Jackson et al.

(10) Patent No.: US 6,880,211 B2
(45) Date of Patent: Apr. 19, 2005

(54) MACRO CLOSURE DEVICE FOR DISPOSABLE ARTICLES

(75) Inventors: Byron M. Jackson, Forest Lake, MN (US); Leigh E. Wood, Woodbury, MN (US); Randall L. Alberg, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 7 days.

(21) Appl. No.: 10/350,204

(22) Filed: Jan. 23, 2003

(65) Prior Publication Data

US 2003/0229975 A1 Dec. 18, 2003

Related U.S. Application Data

(63) Continuation-in-part of application No. 10/170,619, filed on Jun. 13, 2002, now abandoned.

(51) Int. Cl.[7] .......................... A41F 1/00; A44B 17/00; A61F 13/16
(52) U.S. Cl. .................. 24/698.1; 24/579.11; 24/589.1; 24/701; 24/702; 604/361; 604/378; 604/385.16
(58) Field of Search .............................. 24/698.1, 700, 24/701, 702, 651, 579.11, 589.1; 604/385.16, 378, 361

(56) References Cited

U.S. PATENT DOCUMENTS

| | | | | |
|---|---|---|---|---|
| 177,650 | A | * 5/1876 | McMurty | ...................... 24/701 |
| 198,097 | A | 12/1877 | Fries | |
| 207,253 | A | 8/1878 | Chipley | |
| 254,635 | A | * 3/1882 | Gifford | ...................... 24/589.1 |
| 378,874 | A | 3/1888 | Davis | |
| 771,719 | A | 10/1904 | Copeland | |
| 791,654 | A | 6/1905 | Searle | |
| 1,095,947 | A | 5/1914 | Thorp | |
| 1,229,795 | A | * 6/1917 | Sandholzer | ................. 24/589.1 |
| 1,281,613 | A | * 10/1918 | McBreen | ...................... 24/700 |
| 1,427,561 | A | * 8/1922 | Willoughby | ................. 24/700 |
| 1,499,428 | A | 7/1924 | Wagner | |
| 2,076,016 | A | * 4/1937 | Canham | ...................... 24/700 |
| 2,294,617 | A | 9/1942 | Horowitz | |
| 2,548,162 | A | 4/1951 | Karels | |
| 2,787,244 | A | 4/1957 | Hickin | |
| 2,837,096 | A | 6/1958 | Leveillee | |
| 3,121,931 | A | * 2/1964 | Diaz | ......................... 24/698.1 |
| 3,276,944 | A | 10/1966 | Levy | |
| 3,338,992 | A | 8/1967 | Kinney | |

(Continued)

FOREIGN PATENT DOCUMENTS

| | | |
|---|---|---|
| CA | 2128124 | 1/1995 |
| CA | 2240032 | 1/1999 |
| EP | 0 757 550 B1 | 12/1998 |
| GB | 2 328 365 B | 12/1999 |
| WO | WO 96/10481 | 4/1996 |
| WO | WO 97/02795 | 1/1997 |
| WO | WO 97/02797 | 1/1997 |
| WO | WO 97/02799 | 1/1997 |
| WO | WO 99/07319 | 2/1999 |
| WO | WO 00/35395 | 6/2002 |

*Primary Examiner*—Victor Sakran
(74) *Attorney, Agent, or Firm*—William J. Bond

(57) ABSTRACT

There is provided an improved tab member for a closure system comprising a tab portion and a slot member. The slot member includes a slit or a loop, with the slot located between an inboard portion and an outboard portion. The tab portion has a tab member having a length, an inner edge, an outer edge and at least one lip portion. The tab member outer edge is passed through the slot of the slot member to engage the fastening device. Once passed through the slot, at least one lip portion of the tab member overlaps or catches the outboard portion of the slot member to prevent the tab member from disengaging from the slot member. The slot member outward portion is retained between the lip portion (s) and the underlying generally flexible tab carrier substrate.

26 Claims, 15 Drawing Sheets

U.S. PATENT DOCUMENTS

| | | |
|---|---|---|
| 3,341,394 A | 9/1967 | Kinney |
| 3,482,289 A | 12/1969 | Stradella |
| 3,502,538 A | 3/1970 | Petersen |
| 3,502,763 A | 3/1970 | Hartmann |
| 3,542,615 A | 11/1970 | Dobo et al. |
| 3,620,180 A | 11/1971 | Waldes |
| 3,692,618 A | 9/1972 | Dorschner et al. |
| 3,694,867 A | 10/1972 | Stumpf |
| 3,834,824 A | 9/1974 | Jahn |
| 4,001,924 A | 1/1977 | Bengtsson |
| 4,223,059 A | 9/1980 | Schwarz |
| 4,340,563 A | 7/1982 | Appel et al. |
| 4,713,864 A * | 12/1987 | Hess ................. 24/589.1 |
| 4,718,900 A | 1/1988 | Boland et al. |
| 4,906,492 A | 3/1990 | Groshens |
| 4,965,122 A | 10/1990 | Morman |
| 4,981,747 A | 1/1991 | Morman |
| 5,019,071 A | 5/1991 | Bany et al. |
| 5,114,781 A | 5/1992 | Morman |
| 5,116,662 A | 5/1992 | Morman |
| 5,167,897 A | 12/1992 | Weber et al. |
| 5,226,992 A | 7/1993 | Morman |
| 5,300,057 A | 4/1994 | Miller et al. |
| 5,389,438 A | 2/1995 | Miller et al. |
| 5,501,679 A | 3/1996 | Krueger et al. |
| 5,545,159 A | 8/1996 | Lancaster et al. |
| 5,685,758 A | 11/1997 | Paul et al. |
| 5,944,707 A | 8/1999 | Ronn |
| 6,022,431 A | 2/2000 | Blenke et al. |
| 6,075,178 A * | 6/2000 | La Wilhelm et al. ....... 604/361 |
| 6,093,665 A | 7/2000 | Sayovitz et al. |
| 6,102,901 A | 8/2000 | Lord et al. |
| 6,245,050 B1 * | 6/2001 | Odorzynski et al. ... 604/385.16 |
| 6,251,097 B1 | 6/2001 | Kline et al. |
| 6,261,278 B1 | 7/2001 | Chen et al. |
| 6,432,098 B1 | 8/2002 | Kline et al. |

* cited by examiner

MACRO CLOSURE DEVICE FOR DISPOSABLE ARTICLES

CROSS REFERENCE TO RELATED APPLICATIONS

This is a continuation-in-part of application Ser. No. 10/170,619, filed Jun. 13, 2002 abandoned, the disclosure of which is incorporated herein by reference.

FIELD OF THE INVENTION

The present invention relates to closure elements for disposable absorbent articles such as diapers, training pants and incontinence pads. More particularly, the present invention relates to closure elements for disposable absorbent articles which are easy to use and manufacture.

BACKGROUND OF THE INVENTION

Many different types of refastenable closures elements are known, including ties, pins, hook and loop systems, hook and eye systems, buttons, snaps, interlocking shapes, buckles, adhesive tapes, cohesive surfaces, and zippers and other slide connectors. Such fasteners have been used on a variety of products, both durable and disposable. Typical uses include envelopes, clothing, diapers, packages, footwear, construction closures, general attachment needs and feminine hygiene products.

Some fastening devices, such as hook and loop or adhesive tapes, require aligning an engaging surface with a landing surface. While this can result in an effective closure, it often results in misapplication and/or poor alignment of the elements being connected. Further, hook and loop fasteners can become ineffective due to compression and contamination or can harm surrounding materials. With an adhesive system, improperly fastening the device may render the entire product unusable. For example, in diaper applications, repositioning a tape tab which has been fastened improperly may result in tearing the outer cover of the diaper. Further, adhesive systems are prone to contamination-induced performance problems. In order to help prevent such problems, the use of these types of fasteners often require inefficient designs and extra material usage which can add to the cost of the products.

Other systems such as buttons, snaps, hooks and eyes, and ties are limited in that they connect discrete points only. If only one fastening device is used for a particular closure, the connection allows material around the fastener to rotate around the discrete points connected by the fastener. Further, if a span other than a single point needs to be connected, these systems generally require more than one fastening device per closure. Multiple connections can be cumbersome and can result in gapping between the discrete fastening device components, particularly if the connection is under stress. These systems also require precise alignment of the components to create the connection desired. Some point-to-point fastening systems require that forces be maintained on the system throughout the time the fastener is connected.

Other examples of interlocking closures can be found in U.S. Pat. Nos. 198,097; 207,253; 378,874; 771,719; 791,654; 2,837,096; 3,482,289; 3,620,180; 3,834,824 and 4,001,924. All of these fasteners can join lengths or spans, but each suffers from at least one important disadvantage, especially for use with disposable products like diapers. Some require the user to press on the connection to create engagement. Others require intricate manipulation to engage, such as tucking a tab over one element then below another. Yet others require at least one element to deform to create engagement, which may limit the load bearing capability of the fastener. Most lack provisions for allowing the fastener to conform to different shaped surfaces while in use and many of the systems have no provisions allowing for adjustable fit. Further, if used in disposable absorbent products such as diapers, these fasteners can cause skin marking and discomfort for the wearer.

To address these problems, U.S. Pat. No. 6,251,097 discloses a slot and tab closure design wherein the tab hinges are a "T" shape. The tabs are specifically designed for use on disposable diapers, bibs, wraps and packages, as well as sanitary napkins. The tabs taught in this patent contain a "lip" portion, defined as that portion of the tab member 42 which is not joined directly to the underlying structure of the article to which the tab member is attached, and the lip portion lifts away from the underlying structure of the article so that it can be positioned in an overlapping configuration with at least a portion of an outboard portion of a slot member (see, col. 8, lns. 18–39). This lip portion in the tab requires a complex product process as the lip is formed of a separate material attached to the underlying support substrate.

WO 97/02795 discloses a closure system on a diaper, which could also be considered a macro closure. The fastening means is comprised of two mutually co-acting first and second fastener elements and characterized in that the first or the second part of the fastener means includes a fastener portion which projects out in the circumferential direction of the waist band and which can be inserted into an opening in its associated second or first fastener element, and in that one of the first and the second fastener elements includes at least one locking member which extends in a direction generally perpendicular to the direction in which the fastener portion is inserted and co-acts with a locking aperture in the second fastener element when in the inserted position. The closure system requires complex three-dimensional shapes and would be difficult to manufacture and provide in a packaged form with multiple diapers.

U.S. Pat. No. 2,548,162 teaches a pinless diaper that uses what can be called a macro closure system. This system uses tabs and loops and the tabs are heart shaped and the widest part of the tab exceeds substantially in width the base portion (where the tab attaches to the diaper).

U.S. Pat. No. 5,545,159 teaches a disposable diaper with a type of macro closure wherein the macro closure comprises interlocking projections and receptacles. This system is also complex.

There is a need in the art for a macro closure system where the elements are easy to manufacture and use as well as can be packaged into a multi-article pack without creating uniformity problems due to the component having a three dimension shape.

SUMMARY OF THE INVENTION

The present invention is directed at an improved tab member for a closure system comprising a tab portion and a slot member. The slot member includes a slit or a loop, with the slot located between an inboard portion and an outboard portion. The tab portion has a tab member having a length, an inner edge, an outer edge and at least one lip portion. The tab member outer edge is passed through the slot of the slot member to engage the fastening device. Once passed through the slot, at least one lip portion of the tab member overlaps or catches the outboard portion of the slot member to prevent the tab member from disengaging from the slot member. The slot member outward portion is retained between the lip portion(s) and the underlying generally flexible tab carrier substrate.

The improved tab member of the present invention provides an improved solution for a slot and tab closure system. The tab member of the present invention tab portion is a laminate structure with at least one layer in common with the tab carrier substrate so the connection between the tab member and the tab carrier substrate is strong and overall the tab portion is formed of a coplanar laminate so that the tab portion is simple to manufacture.

DETAILED DESCRIPTION OF THE PREFERRED EMBODIMENT

Figure 7:
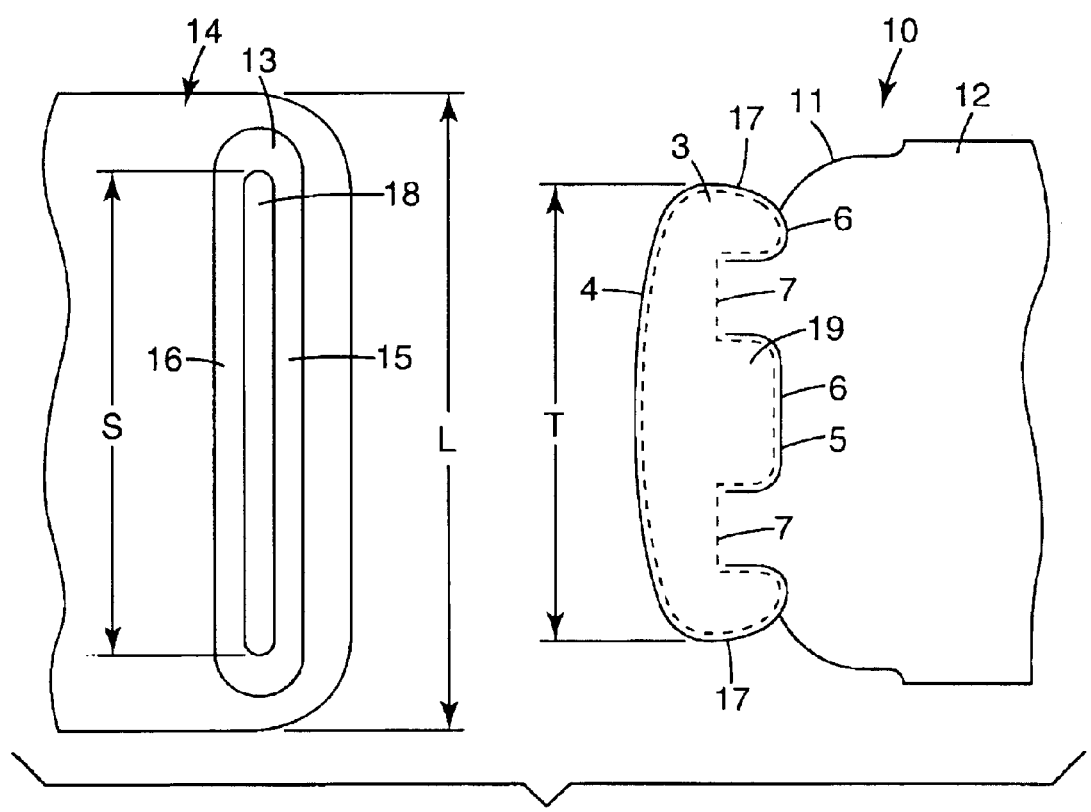
FIG. 7 is a top view of the first embodiment tab portion prior to use in a slot member.

The fastening system of the invention preferably includes a fastening device, which comprises at least a tab portion and a slot member. As shown in FIG. 7, the tab portion 11 preferably includes a generally elongate tab member 3 having an outer edge 4, an inner edge 5, at least one lip portion 6 and a length T and a tab member carrier substrate 12. The slot member 14 includes an inboard portion 16, an outboard portion 15 and a slot 18 disposed between the inboard portion 16 and the outboard portion 15. The slot member 14 has a length L and the slot 18 has a length S, as shown in FIG. 7.

The fastening device 10 is fastened by passing the tab member 3 completely through the slot 18 of the slot member 14. (It is also contemplated that two or more slot members could engage with two or more tab members.) Once the tab member 3 has been passed through the slot 18, as shown in FIG. 7, the lip portion or portions 6 of the tab member 3 rotate into a plane generally parallel with the plane of the slot member 14 such that at least a part of a lip portion 6 overlaps at least a part of an outboard portion 15 of the slot member 14. The lip portion 6 of the tab member 3 in combination with the tab member carrier substrate 12 will prevent the tab member 3 from slipping back through the slot 18 and disengaging the fastening device 10. A portion of the tab member 3 will extend into the slot 18. The material forming the slot 13 will act to resist forces in shear, which tend to direct the tab member 3 and the slot member 14 apart.

As shown in FIG. 7, the tab member 3 is preferably an elongated member having a length T, an inner edge 5, an outer edge 4, and a lip portion 6 generally adjacent at least a portion of the inner edge. The tab member preferably has longitudinal ends 17 and a central region 19. The lip portion 6 is that portion of the tab member 3, which can rotate away from the plane of the tab carrier substrate, wherein layers forming the tab carrier substrate 12 also generally form one or both outer faces of the tab member 3. The lip portion 6 lifts away from the tab member carrier substrate 12 forming a V-shaped catching surface. The bottom leg of the V is formed by the flexible tab carrier substrate 12 and the upper portion of the leg of the V is formed by the more rigid tab member 3. Since the lip portion 6 of the tab member 3 is cut from the carrier substrate, the lip portion 6 and the remaining cutout portion of the tab carrier substrate 12 are reverse mirror images of the other, the bottom leg of the V formed by the remaining carrier substrate is joined to the lip portion of the tab member at their respective terminal edges or ends and along pivot regions 7.

The tab substrate or member 3 may be of any size and/or shape and may be made from any suitable rigid or semi-rigid material. Generally, however, the tab member 3 should be sized to fit through the slot of the slot member with little or no bending or deformation of either component. The shape of the tab member will often be dependent on the end use of the fastening device, but in any case should be aesthetically pleasing, easy to hold and maneuver, and capable of maintaining the device in a fastened configuration throughout the intended period of use when subjected to expected forces and external conditions.

The tab portion may be unitary with the article to which it is attached or may be a separate element joined thereto. The tab portion may be joined to the article at any location. In a disposable absorbent article embodiment, the tab portion may be an extension of the material making up the side panel. In such cases, it may be preferable to provide additional material or to process the material of the side panel so as to change some of its physical properties. The tab portion may be made of the same or different materials than the article to which it is attached, making it easy to match the exact properties of the fastening device to the intended use. Further, the material from which the tab portion carrier substrates and/or tab member is made can be reinforced and/or weakened at certain locations to help provide the desired flexibility and stiffness to the fastening device. Methods of weakening the material include scoring, cutting, thinning, bending, heat treating, chemical treating and the like. Methods of reinforcing include heat or chemical treating the material, adding material, and increasing the thickness and the like.

Figure 1:
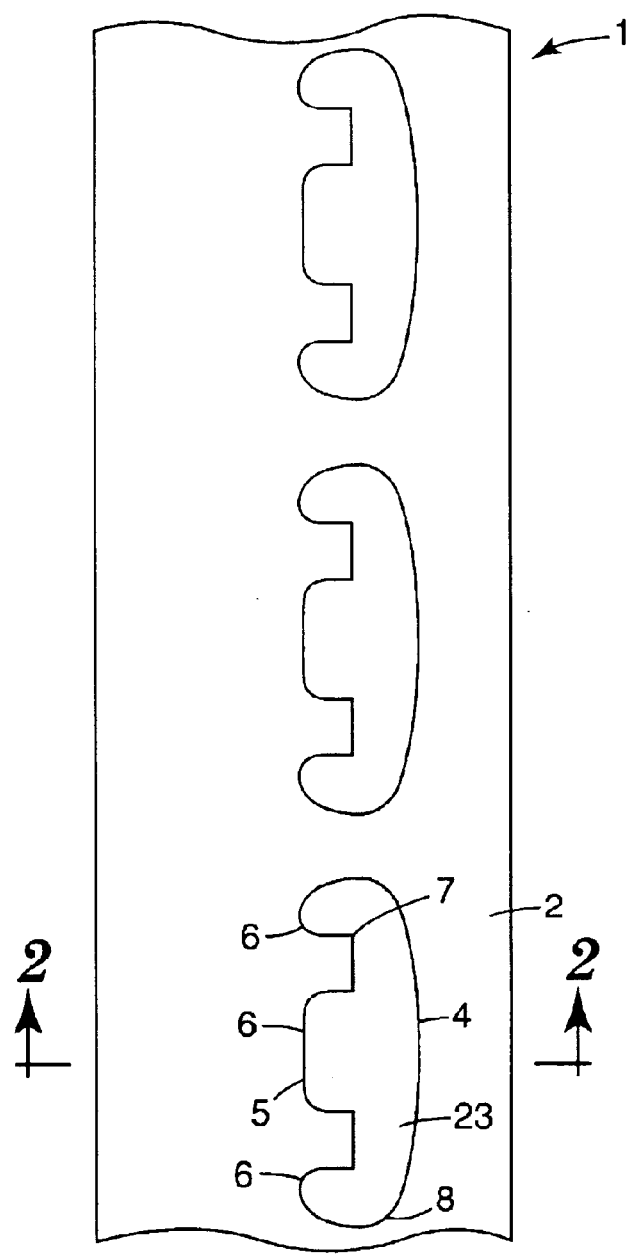
FIG. 1 is a cutaway top view of a first embodiment precursor web with the invention tab portions.

FIG. 1 is a first preferred embodiment of the invention tab portion structure prior to formation in a precursor web 1. At least a semi-flexible tab carrier substrate web 2 is provided. The substrate web 2 can generally have a Gurley stiffness of 1–10 and is preferably formed of a nonwoven, woven or film, or laminate thereof. The overall tab carrier substrate should have a Gurley stiffness of from 1 to 500 and preferably 2 to 200, when used alone or in combination with other substrates or materials. Onto the carrier substrate web 2, are placed various tab member substrate structures 23 which have a rigidity substantially higher than that of the substrate web 2. Generally the tab substrate 23 has a Gurley stiffness so as to provide that the tab member 3 of from 500 to 8000, preferably 1000 to 5000. Generally the tab member has a Gurley stiffness at least two (2) times higher than that of the tab carrier substrate alone, or laminates including the substrate web 2, preferably at least five (5) times greater. The tab substrate is preferably formed out of a thermoplastic polymer which generally would have a thickness of from 0.1 mm to 1.0 mm, preferably 0.2 mm to 0.8 mm. The tab member also preferably has a tensile load at yield between 50 and 250 Newtons for a cross-sectional area of about 8 mm$^2$ and an elongation at yield of between 2% and 20%.

Figure 8:
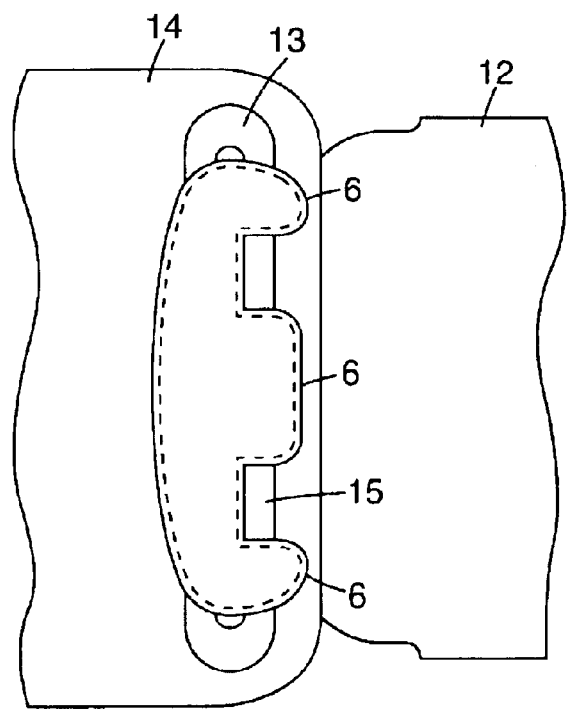
FIG. 8 is a top view of the first embodiment tab portion engaged in a slot member.

The tab substrate 23 shown in FIG. 1 is generally in the form of the final tab member 3 and has an outer edge 4 and an inner edge 5 and ends 8, with a pivot point or region 7 that remains attached to the tab carrier substrate. The outer edge 4 is designed for insertion into a corresponding slot member 14 as disclosed in U.S. Pat. No. 6,251,097 and the inner edge 5 includes one or more lip portions 6 which engage the outboard portion 15 of the slot member when tension is applied to the tab portion in a plane corresponding to the tab substrate web and/or the tab portion. Pivot point or region 7 is located between the outer edge 4 and the outermost edge of the lip portion 6 and is designed to allow the lip portions to move out of the plane with the tab carrier substrate 2 to create a V-shaped gap between the tab carrier substrate 12 and the lip portion 6. The lip portions 6, when out of the plane with the tab carrier substrate 12, engages with the slot structure as shown in FIG. 8. Generally, the lip portion extends at least 3 mm preferable 3 to 10 mm from the pivot point or region 7, most preferably 4 to 8 mm. The portion of the tab member opposite the lip portion, along the pivot region, also preferably will extend at least 2 mm, preferable 3 to 15 mm, from the pivot region, and generally would be at least 20 percent of the lip portion width, preferable at least 50 percent of the lip portion width. This is to provide rotational stability to the engaged tab member, so that when the lip portion is engaged it does not release by rotating around the engaged portion of the slot member when shear forces are applied.

At least one layer of the tab carrier substrate 12 is continuous with a layer of the tab member, at least at the pivot region 7 of the tab member 3. For all constructions preferably one layer, forming a layer of both the tab carrier substrate and the tab member, extends over at least 25 percent of the tab member, preferably at least 50 percent of the tab member and, in a preferred embodiment 100 percent of the tab member and the same layer also extends into at least 10 percent of the tab carrier substrate, preferably at least 25 percent and in a preferred embodiment at least 100 percent of the tab carrier substrate. This allows the tab construction to be stable and provide secure attachment of the tab member to the tab carrier substrate without the need for additional attachment elements such as adhesives, thermal bonding or the like. The tab construction is also easy to manufacture by simple laminating techniques.

The slot member 14 is similarly provided with a substrate web, which has flexibility similar to the tab carrier substrate 12 of the tab portion 11. Preferably, the slot 18 includes a rigidifying element 13 around its periphery, which provides for easier insertion of the tab member and more secure engagement with the tab member 3 lip structure 6 and further defines the slot member outboard and inboard portions 15 and 16. The outboard portion 15 of the slot 18 engages at least one lip portion 6 when the slot member 14 and/or tab portion is placed under tension. The outer edge 4 of the tab member 3 is preferably curved or likewise tapered to allow for easier insertion into the slot 18. Similarly, the lip portion(s) 6 are preferably curved or the like at their ends to ease the initiation of the gripping action with the outboard portion 15 of the slot 18.

For all embodiments, the tab substrates 23 forming the tab members can be joined to the substrate web(s) 2 and/or 9 by the use of adhesives, thermal or ultrasonic bonding, or by melt lamination of thermoplastic tab substrate material preferably onto porous substrate web(s). The substrate webs 2 and 9 as shown are separate webs but a single web could form both layers 2 and 9 where the web is folded adjacent the outer edge of the tab substrate 23. The tab substrate 23 is also preferably directly joined to the substrate web such that a substrate web will form an outer layer of the tab carrier substrate and the tab member creating a tab portion having a uniform outer surface, which in the case of a nonwoven substrate web would have the cloth-like feel of the nonwoven material. Alternatively, woven or film-like materials on laminates could be used as tab substrate webs.

Figure 2:
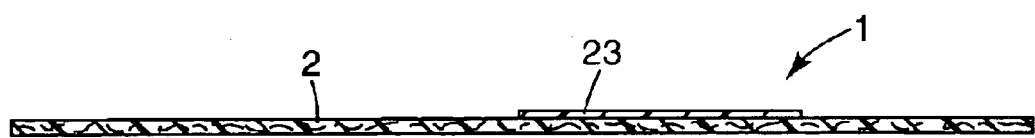
FIG. 2 is a side view of FIG. 1.
Figure 3:
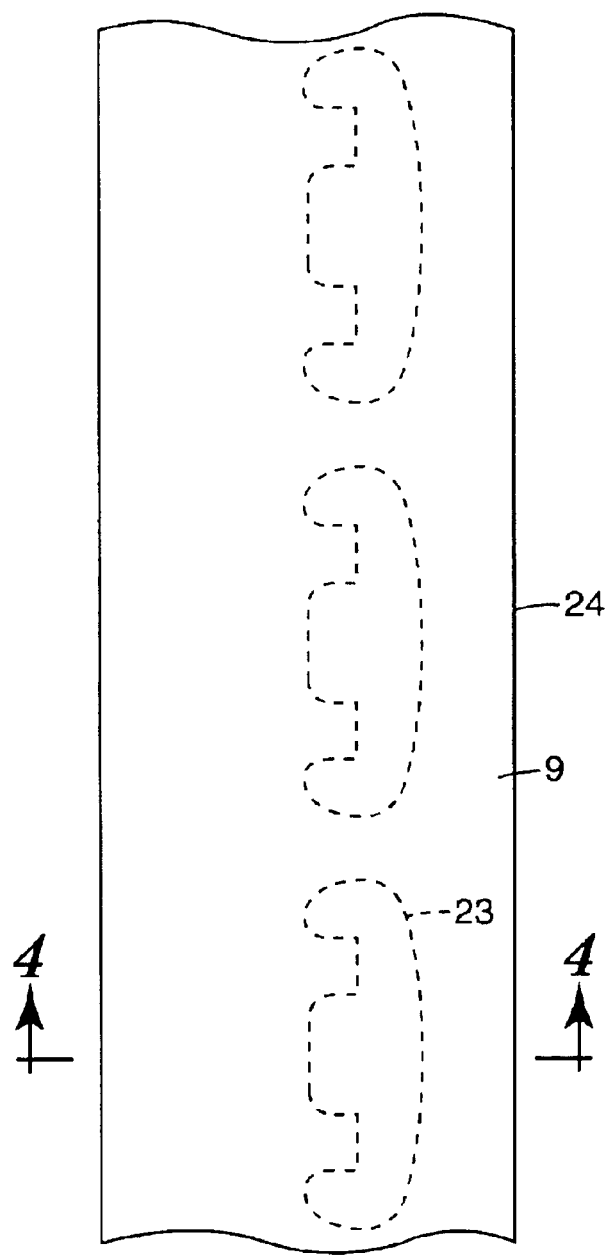
FIG. 3 is a cutaway top view of a first embodiment precursor web with the invention tab portions.
Figure 4:
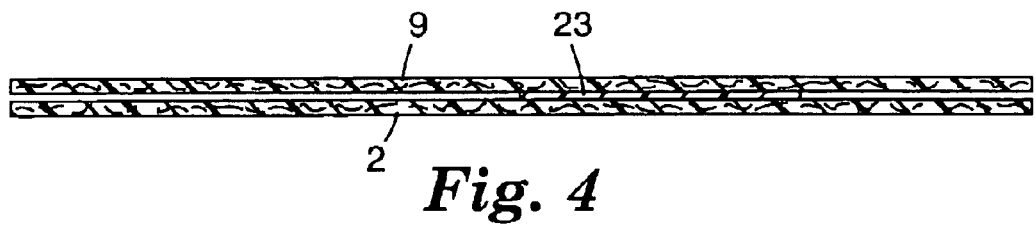
FIG. 4 is a side view of FIG. 3.
Figure 6:
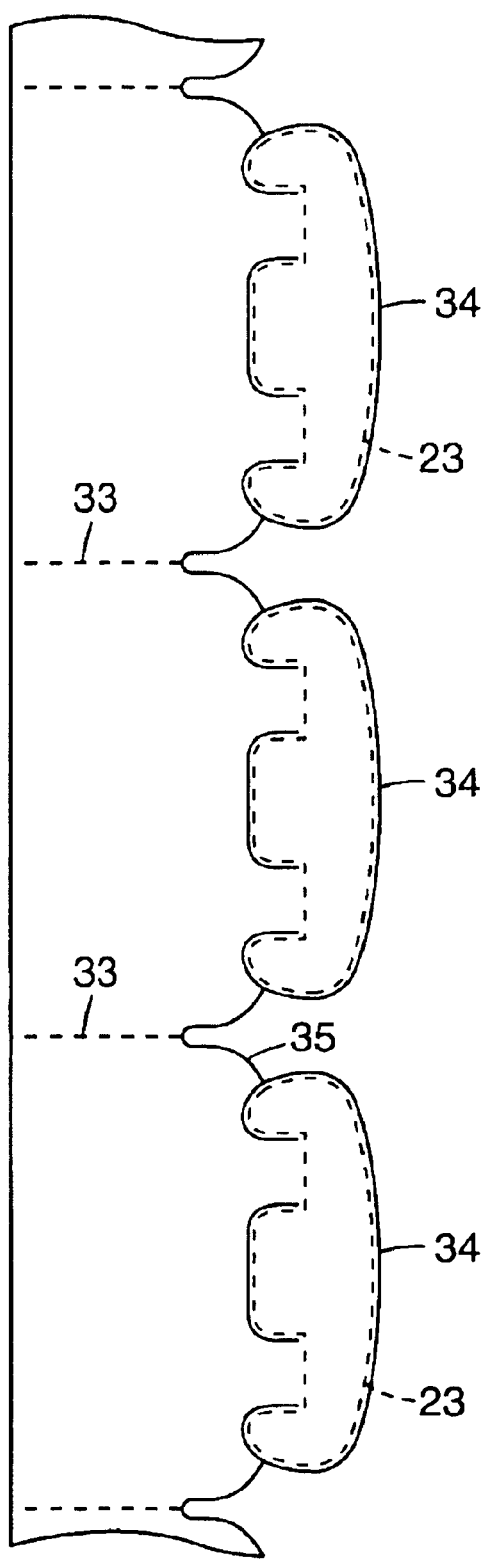
FIG. 6 is a top view of the FIG. 5 material with a trim portion removed.

The precursor material of FIGS. 1 and 2 is then preferentially joined to a second tab substrate web 9 as shown in FIGS. 3 and 4 where the two substrate webs are joined together by conventional lamination methods such as sonic bonding, adhesives, heat bonding, needle tacking or the like. The substrate web(s) and the tab substrate as shown are all mutually coplanar resulting a material having a relatively flat profile. The two webs 2 and 9 would preferably be joined together adjacent the inner edge 5 of the tab substrate 23 or tab member 3. The second substrate web 9 would likewise preferably be joined to an opposing outer face of the tab substrate 23 and could be formed of a like or similar material as substrate web 2. The individual tab portions then could be cut from the precursor tab portion web 24 into the final form as shown in FIG. 6 by a suitably shaped knife blade or die or alternatively the tab could be partially cut from the finished precursor tab portion web 24, as will be described in more detail below.

Figure 5:
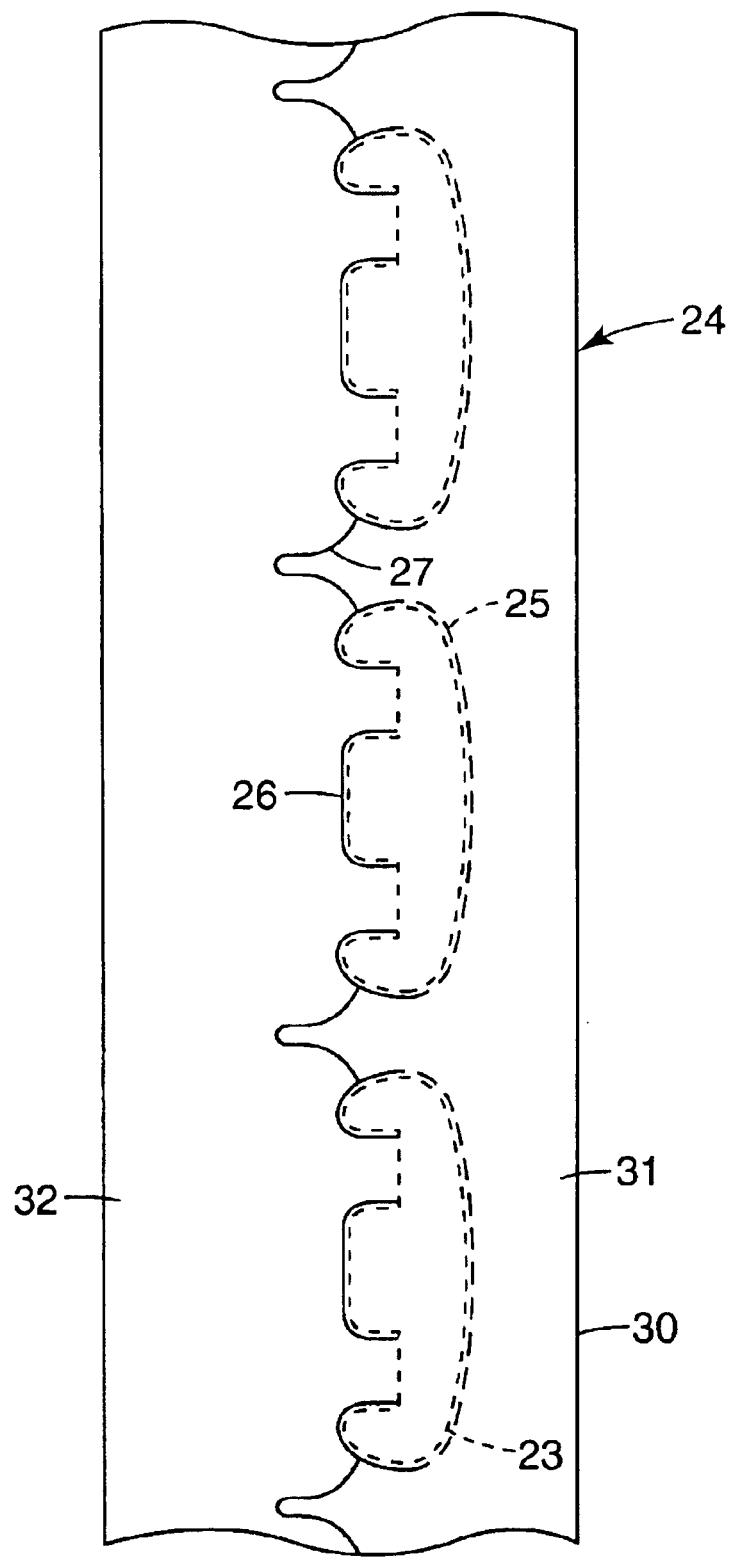
FIG. 5 is a cutaway top view of a first embodiment precursor web with the invention tab portions.

FIG. 5 shows a laminate with a knife blade cut or die-cut suitable for partial trimming of the tab portions from a precursor tab portion web 24 so as to allow the formation of cut precursor tab portion web 24 where the tab portions are partially defined. The dotted or serrated lines 25 represent a perforated or serrated edge cut and the continuous lines 26 and 27 represent continuous knife blade or die edge cut. The curved continuous lines 26 represent continuous cutouts defining the lip portions of the tab member whereas the serrated line 25 represents a cutout for the outer edges of the tab member. Alternatively the serrated cut portion 25 could be continuous. This would provide a continuous cut along an outer edge of the tab substrate web, which would allow removal of a waste edge trim 31 from the precursor tab portion web 24. With the serrated knife blade or die, this edge trim 31 can remain allowing the partially cut web to remain a continuous rectilinear web 30, which facilities even winding of the web into a roll form without formation of raggedy edges in the roll. The tapered continuous cut 27 can be of any suitable size or shape and merely defines the upper leading edge of the tab carrier substrate adjacent the tab member 3. FIG. 5 shows a tab substrate web 30, which has been cut by the knife blade or die. The portion 31 can either remain on the web leaving portion 32 or be subsequently removed such as shown in FIG. 6 where additional serrated cut lines 33 are shown which separates the individual tab portions 34. Shoulders 35 correspond to the knife blade cut 27. The tab substrate(s) 23 is sandwiched between two layers of the substrate webs 2 and 9. If the lines 33 are serrated, the individual tab portions are continuously separable from the web structure. The tab portions can subsequently be manually or automatically separated along the serrated edges 33 when needed. Alternatively, lines 33 could be continuous cuts made by the user of the tabs at the point of use. Preferably the cut around the tab members is outside the area containing the tab substrate at least at the outer edge of the tab substrate so that a tab substrate web edge extends out beyond the more rigid tab substrate by at least 0.5 mm. This softens the tab substrate edge making it more skin friendly.

Figure 17:
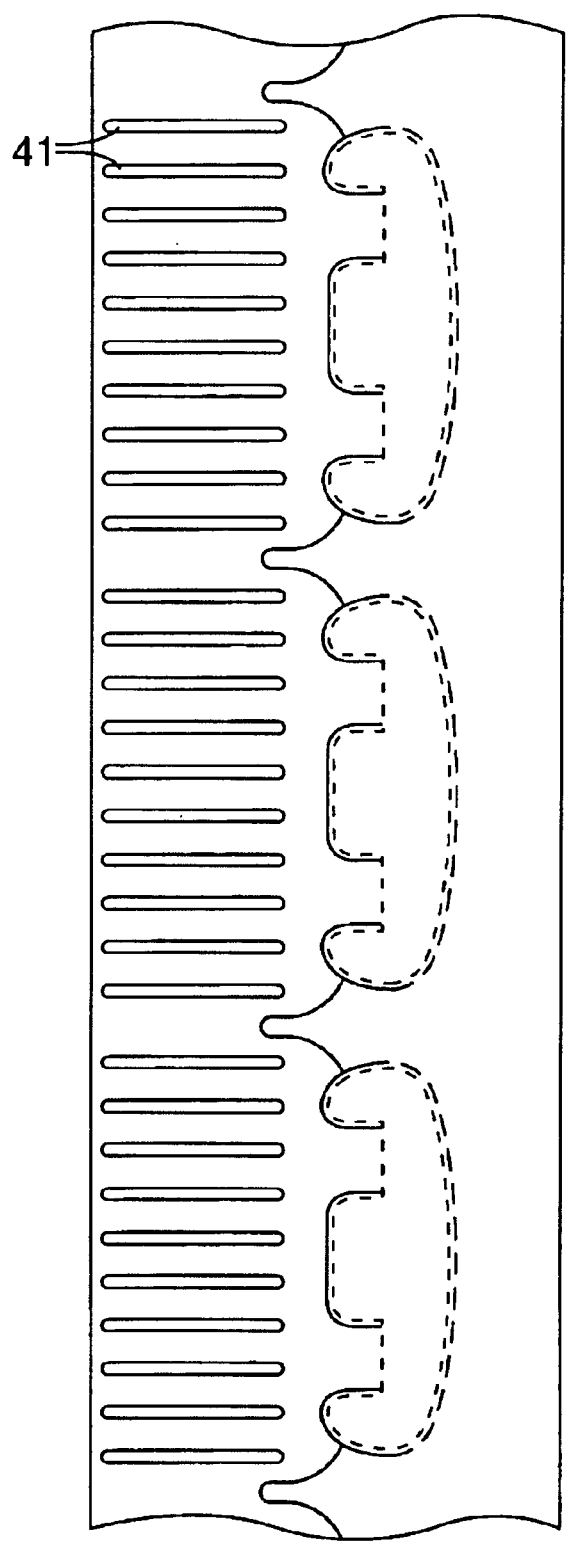
FIG. 17 is a cutaway top view of a second embodiment precursor web of tab portions.

FIG. 17 shows a second embodiment of the invention similar to that shown in FIGS. 1–8 where elastic strand structures 41 are provided on the substrate web 2 and/or 9 to provide for an elasticized or elasticizable structure. In a preferred embodiment, the elastic strands are printed onto either web 2 or 9 in accordance with U.S. patent application Ser. No. 10/012,698, the substance of which is incorporated herein by reference by its entirety, and produced as show and described in FIG. 20. The applied elastic strands can then be elasticized by suitable permanent deformation or elongation of the substrate webs 2 and/or 9 by any suitable elongation means such as interengaging rolls, external tension or the like. Alternatively, the substrate webs 2 and 9 could be made extensible by suitable methods as described below, or are provided as extensible when coated with the elastic strands.

Figure 21:
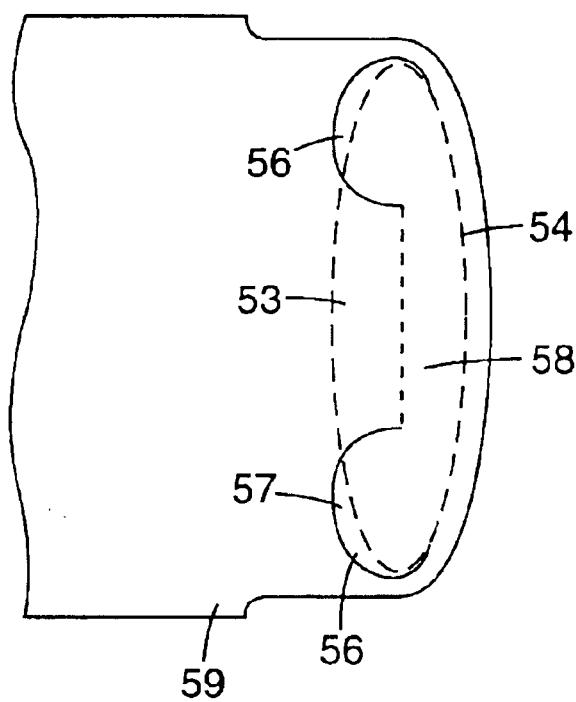
FIG. 21 is a schematic view of a third embodiment of an invention tab portion.

FIG. 21 shows a third embodiment of the invention tab portion structure where a tab substrate 54 is in a form without predefined lip portions and the lip portions 56 are formed by a cutout edge 57. The remaining tab substrate 53 remains integral with the tab carrier substrate 59 where the inner edges of the lip portion cut-outs are preferably provided with a crease or indent 58 to allow the tab to bend or hinge out of the plane of the carrier substrate, for engagement of the lip portions 56 with a corresponding slot.

Figure 9:
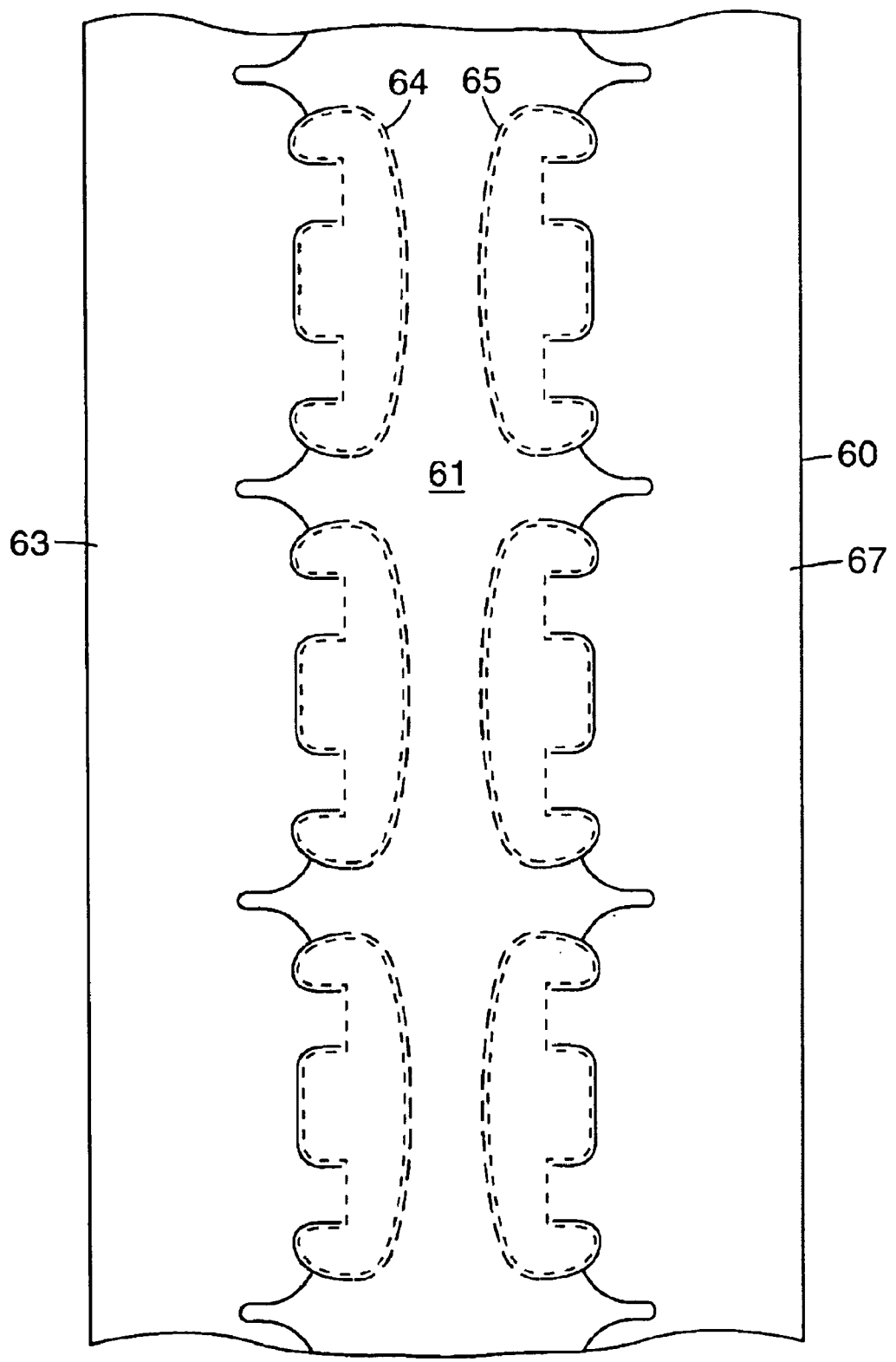
FIG. 9 is a cutaway top view of an alternative fourth embodiment of the first embodiment tab portions on a different precursor web.

FIG. 9 shows an alternative embodiment of a precursor web of the first embodiment tab portion where mirror image tab portions are provided on a single precursor tab portion web 60. As shown in FIG. 9 mating precursor tab portions 63 and 67 are mirror image reflections of each other however they could also be offset or provided at other locations along the lengthwise direction of the completed precursor tab portion web. The center strip 61 can be subsequently removed along the perforated edges 64 and 65, where the continuous lines represent continuous cuts as per the description relative to FIG. 5.

Figure 10:
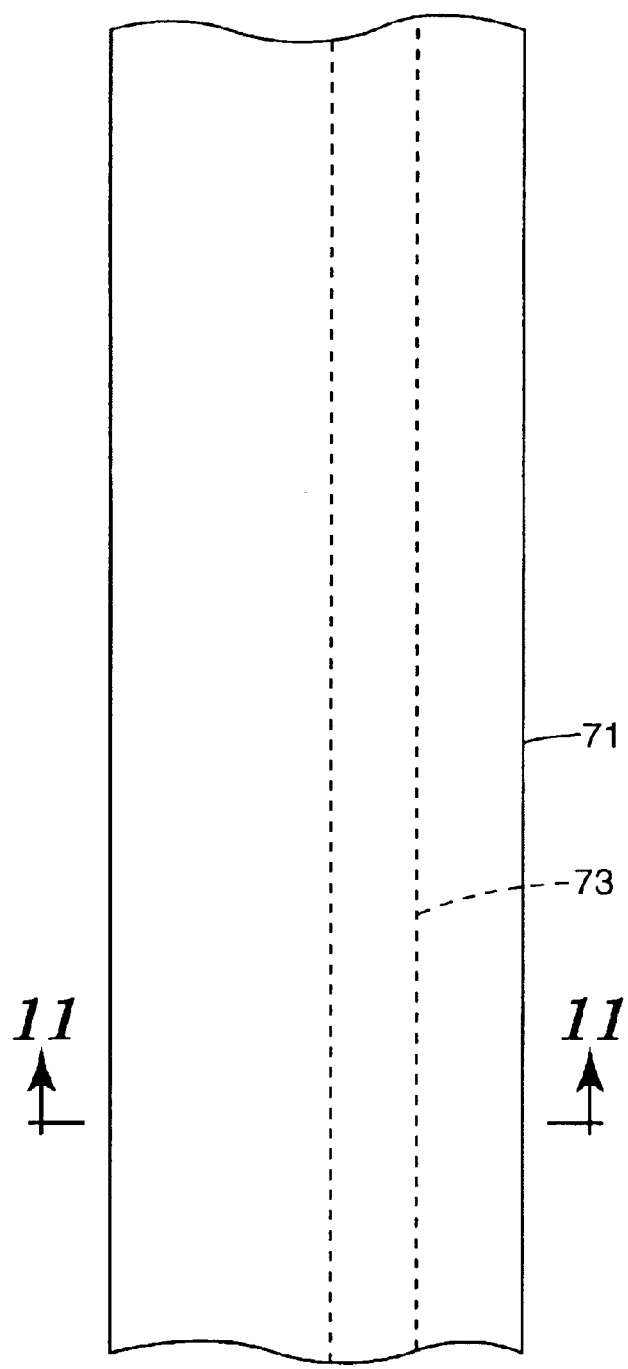
FIG. 10 is a cutaway top view of a fifth embodiment of an invention precursor web of tab portions.
Figure 11:
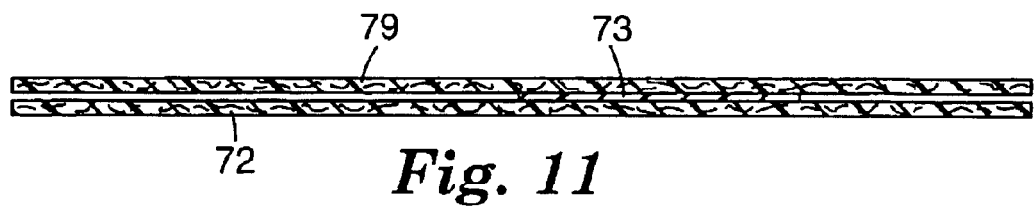
FIG. 11 is a side view of FIG. 10.
Figure 12:
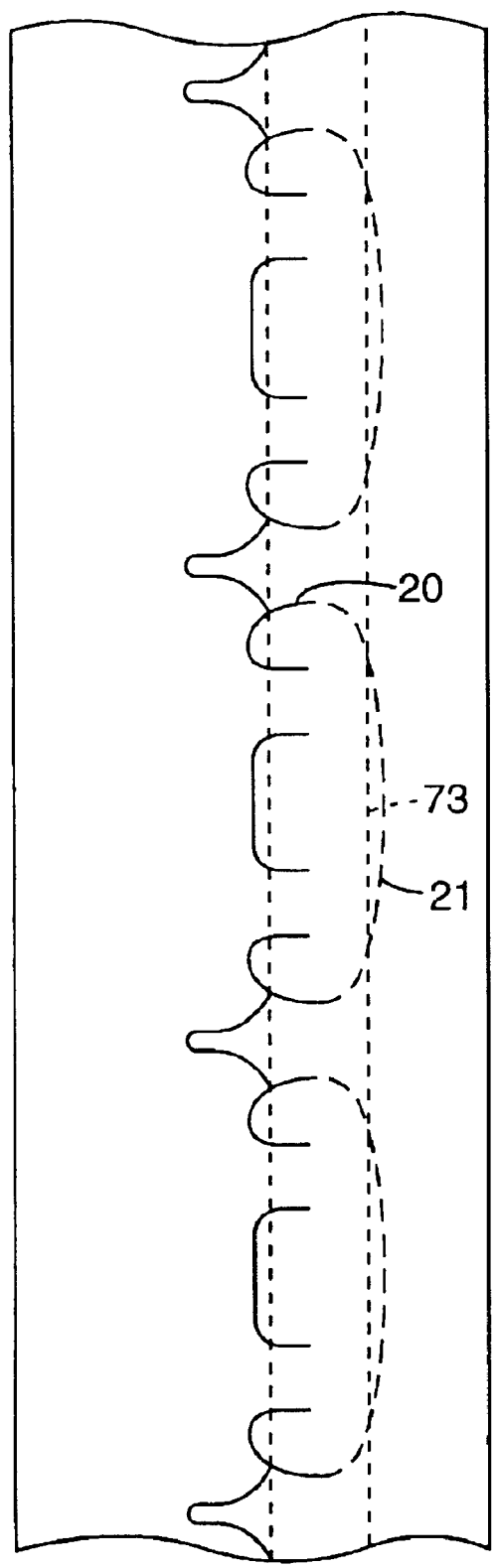
FIG. 12 is a cutaway top view of the FIG. 9 embodiment with the tab portions partially cut from the precursor web.
Figure 13:
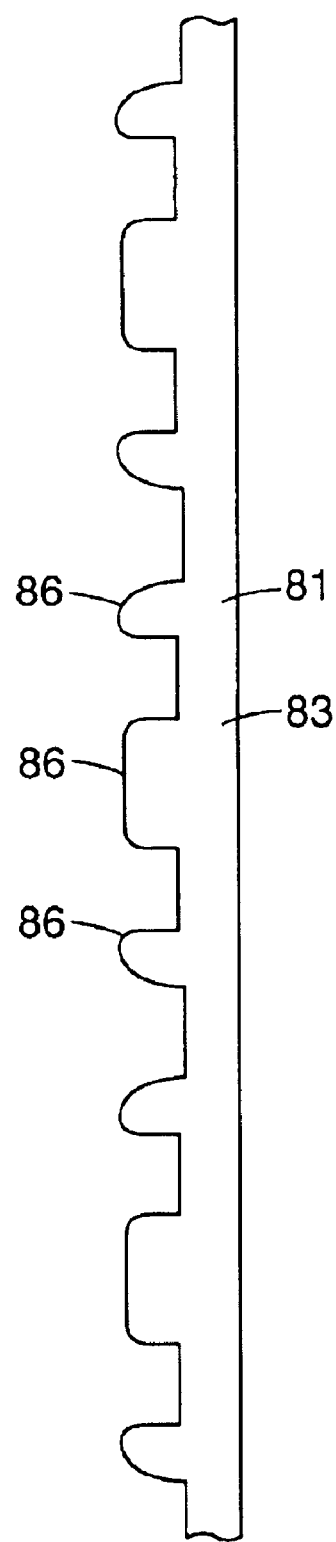
FIG. 13 is a top view of a sixth embodiment tab substrate for use in a precursor web.
Figure 14:
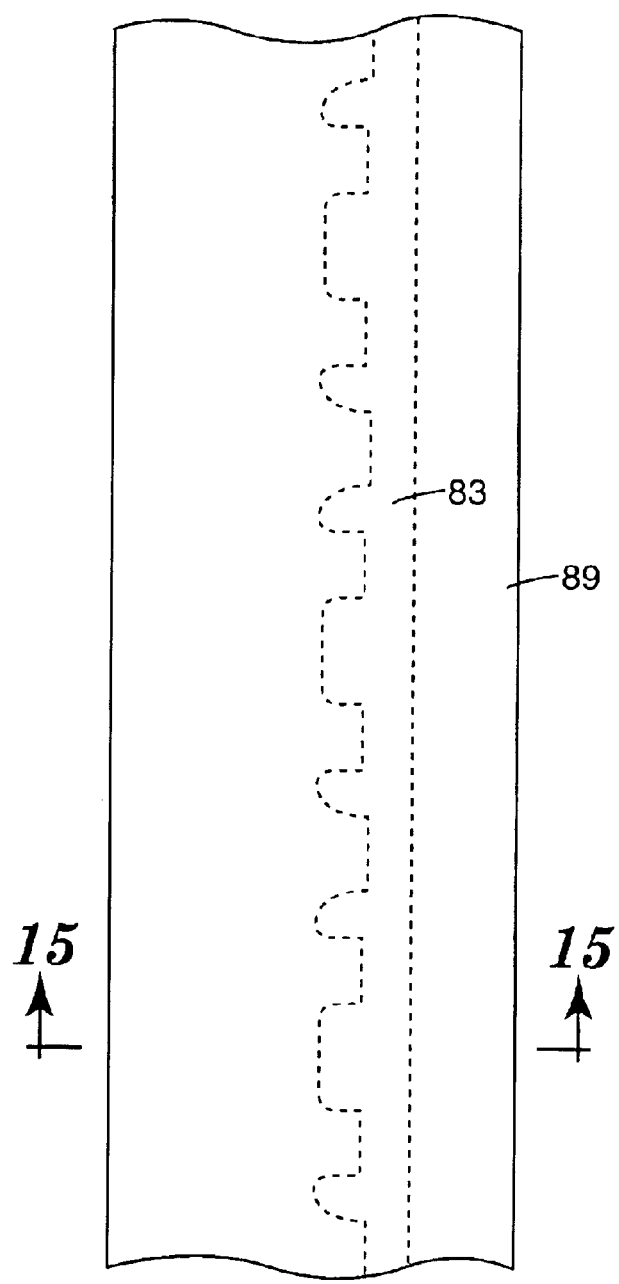
FIG. 14 is a top view of the sixth embodiment tab substrate in a precursor web.

FIGS. 10 and 11 show a fifth embodiment of an invention precursor tab portion web where a continuous strip of a tab substrate 73 is laminated between substrate webs 72 and 79. The particular tab members can then be formed or defined in part by the knife blade or die (such as shown in embodiment of FIG. 5) cuts, as shown in FIG. 12. Numeral 20 designates the continuous knife blade or die cuts of the tab carrier substrate 71 and the tab substrate 73 and 21 represents serrated cuts as per the FIG. 5 embodiment. In this embodiment, the tab substrate could also be an extra layer of substrate web 72 or 79 that has been folded onto itself or the other substrate web or both, and laminated by adhesives ultrasonic or heat. In one case, a single substrate web 72 or 79 could be used and folded over onto itself and laminated to itself to form a tab substrate. In this definition of tab substrate includes a separately applied strip of material or a laminate of an extra folded portion of a substrate web 72 or 79.

Figure 15:
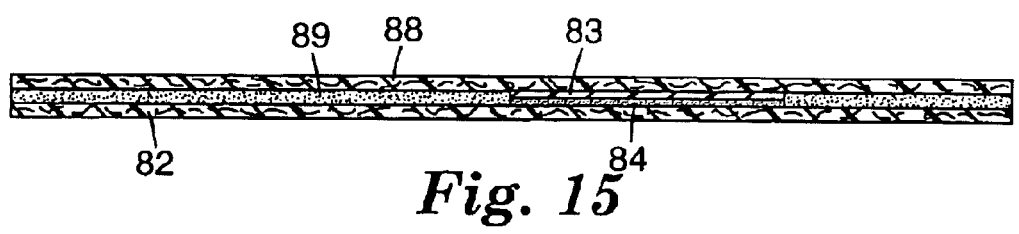
FIG. 15 is a side view of FIG. 14.
Figure 16:
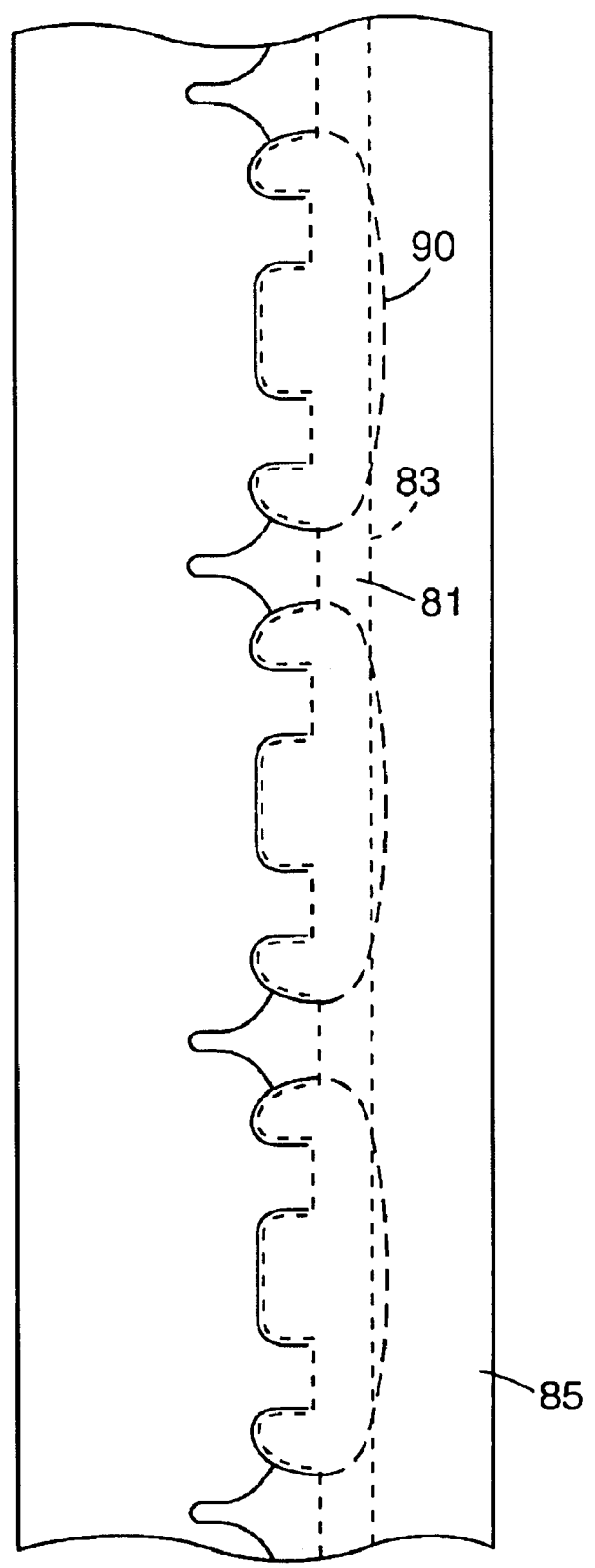
FIG. 16 is a cutaway top view of the FIG. 14 embodiment with the tab portions partially cut from the precursor web.

FIGS. 13–16 show a sixth embodiment of the invention where a continuous tab substrate 83 is joined to substrate webs where on one edge of the continuous tab substrate 83 the lip portions 86 are preformed. The tab substrate 83 has connecting portions 81 separating the yet to be formed tab member. FIG. 15 shows the tab substrate 83 joined between two substrate webs 82 and 88 by use of pressure-sensitive adhesives 89 and 84. As shown in FIG. 16, the tab portions 90 would be partially formed by the use of a cut-out blade or die, as shown in embodiment of FIG. 5 for example, followed by separating the individual tab portions and discarding the connecting portions 81 and trim 85. Use of continuous tab substrates as per this embodiment are generally less advantageous than the use of discrete tab substrate materials. With continuous tab substrates at least a portion of the tab substrate will extend to terminal portion of the side edges of the tab members which tends to create sharp edge which might be perceived as undesirable or not skin friendly. Also, tab substrate material between the tab member is discarded, which is more costly in terms of material waste.

Figure 22:
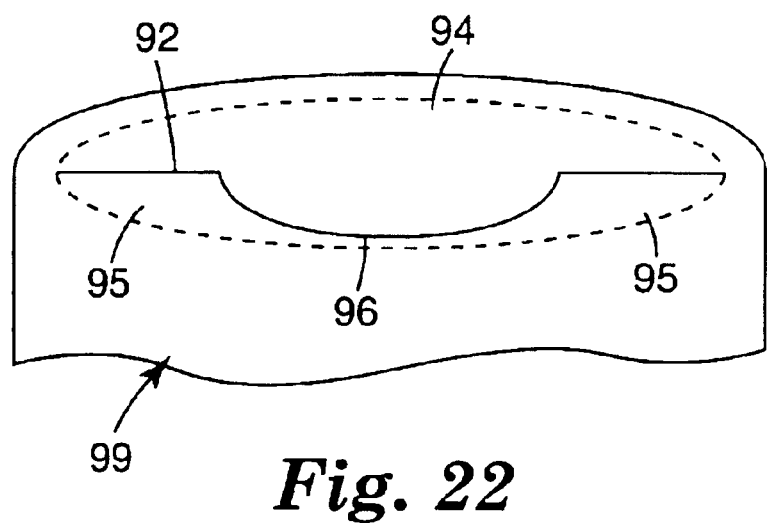
FIG. 22 is a schematic view of a seventh embodiment of an invention tab portion.

FIG. 22 shows a seventh embodiment of the invention tab portion where a tab substrate 94 is joined to substrate webs 99, as shown in FIG. 21, however, where only a single lip portion 96 is formed by die cutting or the like along line 92. Portion 95 of tab substrate 94 becomes detached as shown.

Figure 18:
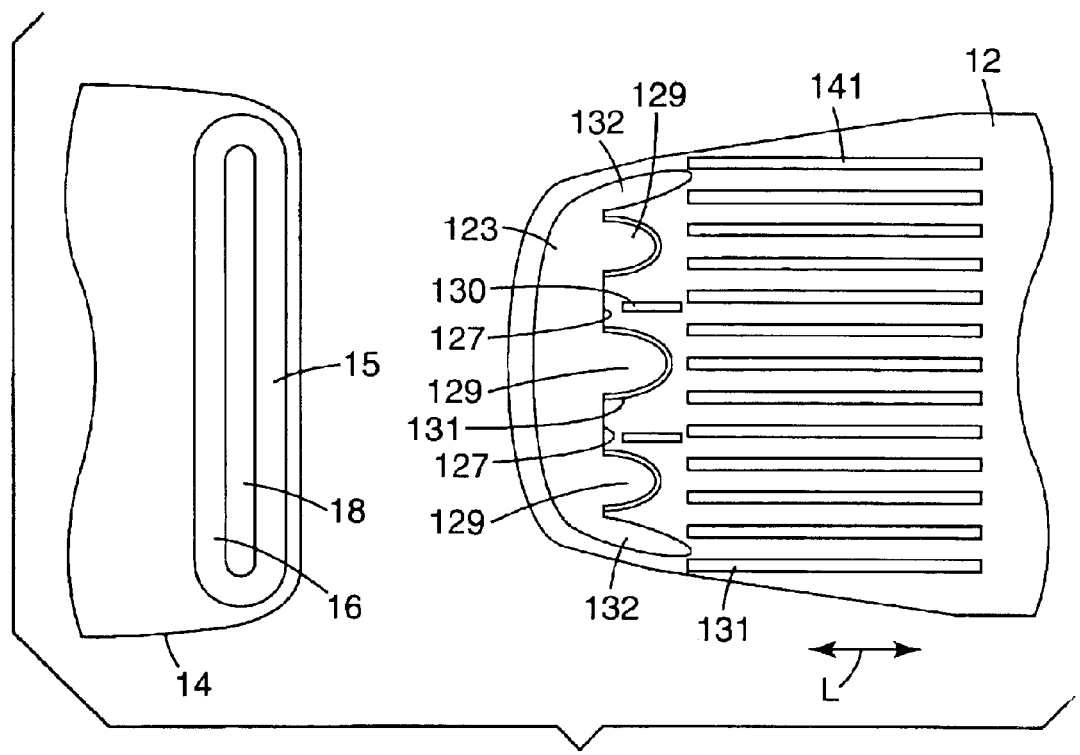
FIG. 18 is a top view of an eighth embodiment of an invention tab portion prior to use with a slot member.
Figure 19:
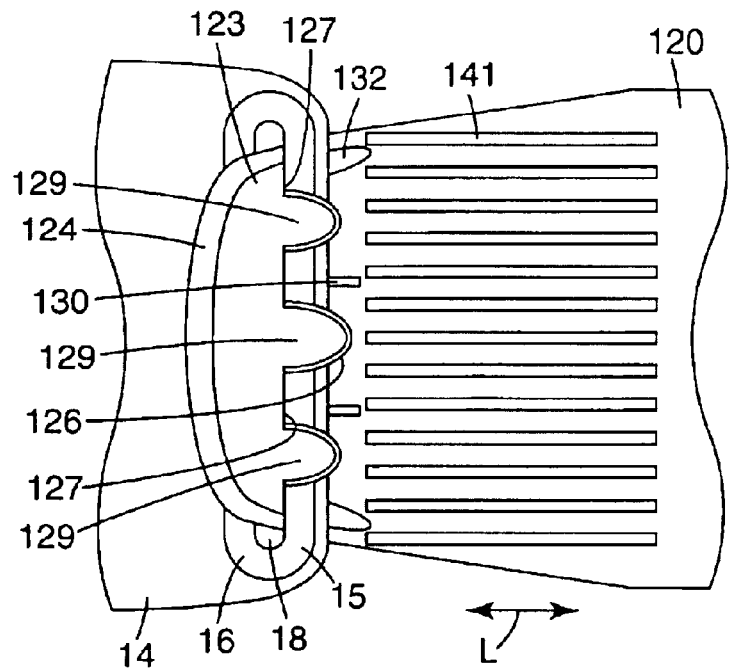
FIG. 19 is a top view of the eighth embodiment tab portion in use with a slot member.

In the FIG. 18 embodiment, the fastening device is fastened by passing the tab member 123 completely through the slot 18 of the slot member 14. Once the tab member 123 has been passed through the slot 18, as shown in FIG. 19, the lip portion or portions 129 of the tab member 123 rotate into a plane generally parallel with the plane of the slot member 14 such that at least a part of a lip portion 129 overlaps at least a part of an outboard portion 15 of the slot member 14. The lip portion(s) 129 of the tab member 123 in combination with the remaining tab member carrier substrate 12 attached to the tab member 123 will prevent the tab member 123 from slipping back through the slot 18 and disengaging the fastening device. A portion of the tab member 123 will extend into the slot 18. The material forming the slot 13 will act to resist forces in shear, which tend to direct the tab member 123 and the slot member 14 apart.

As shown in FIGS. 18 and 19, the tab member 123 is preferably an elongated member having wing elements 132 that remain integral with the carrier substrate 12 attached to the tab member 123. The wing elements 132 prevent slippage of the tab member in the slot while increasing the gripping action of the tab member lip portion(s) 129. The wing element 132 must be able to twist or bend along the pivot region 127 so as to allow the lip portion 129 to rotate away from the plane of the tab carrier substrate. The wing elements 132 can be made to bend by mechanical folding if needed to help the lip portions pivot away from the carrier substrate. Alternatively, a crease can be formed by scoring or other known methods, creating a weakened zone by decreasing the wing element thickness along pivot line or region 127. The wing elements 132 are generally provided along one or both outermost side edges of the tab member 123 outside of the tab member 123 region having the lip portion (s) 129 and are at least partially coextensive with the lip portion(s) 129 in the lengthwise direction L of the tab portion (i.e., in the region of the attached carrier substrate 12). The wing elements 132 also remain integral with the carrier substrate 12 in the main body of the tab portion. As in the other embodiments, layers forming the tab carrier substrate 12 also generally form one or both outer faces of the tab member 123. The lip portion 129 lifts away from the tab member carrier substrate 12 forming a V-shaped catching surface between the lip portion 129 and the substrate 12 and wing elements 132. The bottom leg of the V is formed by the flexible tab carrier substrate 12 and wing elements 132. The upper portion of the leg of the V is formed at least by the more rigid tab member 123. Since the lip portion 129 of the tab member 123 is cut from the carrier substrate along lines 131, the lip portion 129 and the remaining cutout portion of the tab carrier substrate 12 are reverse mirror images of the other, the bottom leg of the V formed by the remaining carrier substrate is joined to the lip portion of the tab member at their respective terminal edges or ends and along pivot regions 127.

Preferably the tab substrate material can be provided with elastic or inelastic reinforcing elements 141 printed on the carrier substrate as per the FIG. 17 embodiment. These elements prevent distortion of the tab substrate material when force is applied to the tab portion in the lengthwise direction L. These reinforcing elements preferably extend into the region of the tab portion containing the wing elements 32 in the lengthwise direction L so that forces applied to the tab portion in the lengthwise direction L are transferred from the reinforcing elements 141 to the wing portions, with no unreinforced carrier substrate 12 between the terminal end of the wing portion 132 and the terminal ends of the reinforcement elements in the lengthwise direction L. Preferably the reinforcing elements and the wing portions will overlap by at least 1 mm or more, preferably 2 mm or more. Additional reinforcing elements 130 could also be provided in the tab region between the wing portions 132 to provide further reinforcement of weak carrier substrate 12 material, if needed. This additional reinforcement element 30 preferably could also overlap with elements 141, or be an extension of the elements 141 and could extend up to, or be integral with, the tab member 123.

The substrates which can be used in connection with the present invention may have a variety of constructions. For example, the substrates may be a woven material, nonwoven material, knit material, paper, film, or any other continuous media. The substrates may have a wide variety of properties, such as extensibility, elasticity, flexibility, conformability, breathability, porosity, stiffness, etc. Further, the substrates may include pleats, corrugations or other deformations from a flat planar sheet configuration.

Suitable processes for making a nonwoven web that may be used in connection with the present invention include, but are not limited to, airlaying, spunbond, spunlace, bonded melt blown webs and bonded carded web formation processes. Spunbond nonwoven webs are made by extruding a molten thermoplastic, as filaments from a series of fine die orifices in a spinneret. The diameter of the extruded filaments is rapidly reduced under tension by, for example, by non-eductive or eductive fluid-drawing or other known spunbond mechanisms, such as described in U.S. Pat. Nos. 4,340,563; 3,692,618; 3,338,992 and 3,341,394; 3,276,944; 3,502,538; 3,502,763 and 3,542,615. The spunbond web is preferably bonded (point or continuous bonding).

The nonwoven web layer may also be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation.

Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Meltblown nonwoven webs may be formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength for the present invention, meltblown webs must be further bonded such as by through air bonding, heat or ultrasonic bonding as described above.

A web can be made extensible by skip slitting as is disclosed in, e.g., International Publication No. WO 96/10481. If an elastic, extensible web is desired, the slits are discontinuous and are generally cut on the web prior to the web being attached to any elastic component. Although more difficult, it is also possible to create slits in the nonelastic web layer after the nonelastic web is laminated to the elastic web. At least a portion of the slits in the nonelastic web should be generally perpendicular (or have a substantial perpendicular vector) to the intended direction of extensibility or elasticity (the at least first direction) of the elastic web layer. By generally perpendicular it is meant that the angle between the longitudinal axis of the chosen slit or slits and the direction of extensibility is between 60 and 120 degrees. A sufficient number of the described slits are generally perpendicular such that the overall laminate is elastic. The provision of slits in two directions is advantageous when the elastic laminate is intended to be elastic in at least two different directions.

A nonwoven web used in connection with the present invention can also be a necked or reversibly necked nonwoven web as described in U.S. Pat. Nos. 4,965,122;

4,981,747; 5,114,781; 5,116,662; and 5,226,992. In these embodiments the nonwoven web is elongated in a direction perpendicular to the desired direction of extensibility. When the nonwoven web is set in this elongated condition, it will have stretch and recovery properties in the direction of extensibility.

Figure 20:
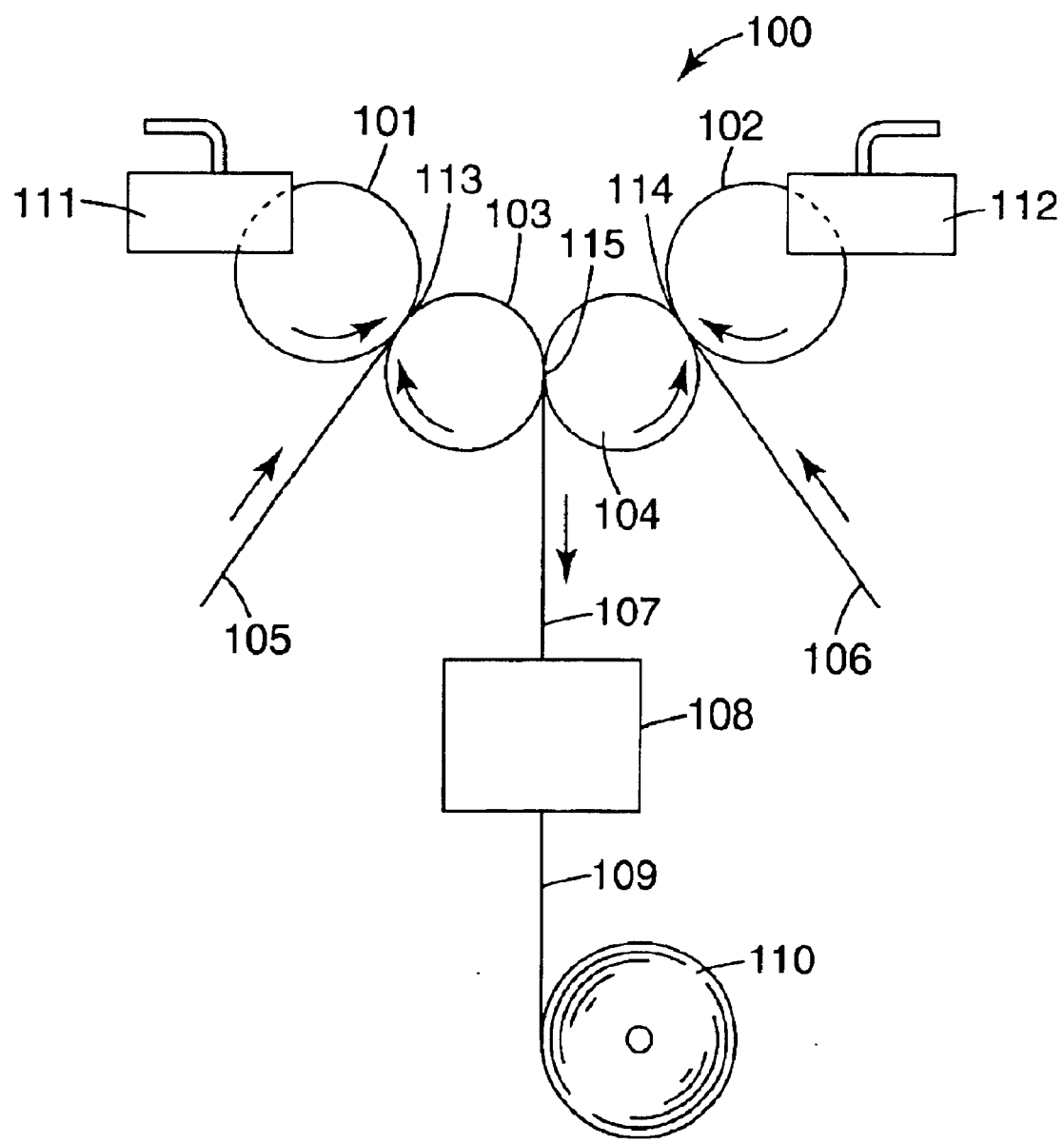
FIG. 20 is a schematic view of a process useful in forming the invention tab portion precursor webs.

The substrates may preferably exhibit some porosity on one or both of the major surfaces of the substrate such that when the tab substrate is formed by printing a molten thermoplastic composition as shown in FIG. 20, a mechanical bond is formed between the molten thermoplastic composition and the substrate as the molten thermoplastic composition infiltrates and/or encapsulates a portion of the porous surface of the substrate. As used in connection with the present invention, the term "porous" includes both structures that include voids formed therein, as well as structures formed of a collection of fibers (e.g., woven, nonwoven, knit, etc.) that allow for the infiltration of molten thermoplastic composition into the interstices between fibers. If the porous surface includes fibers, the thermoplastic composition may preferably encapsulate fibers or portions of fibers on the surface of the substrate.

The type and construction of the material or materials in the substrate should be considered when selecting an appropriate substrate to which a molten thermoplastic composition is applied. Generally, such materials are of the type and construction that do not melt, soften, or otherwise disintegrate under the temperatures and pressures experienced during the step of transferring the thermoplastic composition to the substrate. For example, the substrate should have sufficient internal strength such that it does not fall apart during the process. Preferably, the substrate has sufficient strength in the machine direction at the temperature of the transfer roll to remove it intact from the transfer roll.

Although the substrates depicted in the various cross-sectional views of the articles manufactured according to the methods of the present invention are illustrated as single layer structures, it should be understood that the substrates might be of single or multi-layer construction. If a multi-layer construction is used, it will be understood that the various layers may have the same or different properties, constructions, etc.

The tab substrates are preferably formed of a wide variety of different thermoplastic material and preferably nonelastomeric thermoplastic polymeric materials. As used in connection with the present invention, "thermoplastic" (and variations thereof) means a polymer or polymeric composition that softens when exposed to heat and returns to its original condition or near its original condition when cooled to room temperature. Preferred thermoplastic compositions are those that are melt processable. Such polymers are those that will flow, yet not significantly degrade during a melt process.

Some examples of nonelastomeric thermoplastic compositions that may be used in connection with the present invention include, but are not limited to, polyurethanes, polyolefins (e.g., polypropylenes, polyethylenes, etc.), polystyrenes, polycarbonates, polyesters, polymethacrylates, ethylene vinyl acetate copolymers, ethylene vinyl alcohol copolymers, polyvinylchlorides, acrylate modified ethylene vinyl acetate polymers, ethylene acrylic acid copolymers, nylons, fluorocarbons, or blends or copolymers thereof, etc.

A nonelastomeric thermoplastic polymer is one that melts and returns to its original condition or near its original condition upon cooling and which does not exhibit elastomeric properties at ambient conditions (e.g., room temperature and pressure). As used in connection with the present invention, "nonelastomeric" means that the material will not substantially resume its original shape after being stretched. Further, the nonelastomeric materials may preferably sustain permanent set following deformation and relaxation, which set is preferably at least about 20 percent or more, and more preferably at least about 30 percent or more of the original length at moderate elongation, e.g., about 50% (for those materials that can even be stretched up to 50% without fracture or other failure).

The nonelastomeric thermoplastic compositions used in connection with the present invention can also be combined with various additives for desired effect. These include, for example, fillers, viscosity reducing agents, plasticizers, tackifiers, colorants (e.g., dyes or pigments), antioxidants, antistatic agents, bonding aids, antiblocking agents, slip agents, stabilizers (e.g., thermal and ultraviolet), foaming agents, microspheres, glass bubbles, reinforcing fibers (e.g., microfibers), internal release agents, thermally conductive particles, electrically conductive particles, and the like. The amounts of such materials that can be useful in the thermoplastic compositions can be readily determined by those skilled in the art of processing and using such materials.

In forming discrete tab substrates of thermoplastic material, the process depicted in FIG. 20 can be used. In this process, a transfer tool 101 or 102 that can be used to deposit the tab substrate. The transfer tools 101 and/or 102 generally include a depression formed therein. The depressions can be of the form of the tab substrate or other elements or multiple depressions can form the tab substrate or the like. The depressions can be of the same size or of differing sizes dispersed over the surface of the transfer rolls 101 or 102, both in terms of footprint as well as depression volume. The depressions used to form the tab substrate is preferably a composite of cells or smaller depressions formed in the surface by any suitable technique, e.g., machining, etching, laser ablation, etc.

The depressions on transfer rolls 101 or 102 used in connection with the present invention may be characterized in terms of the area occupied by their footprint on the exterior surface of the forming tool, a maximum dimension of the footprint (in any direction on the surface of the roll), the volume of the depression, the shape of the footprint, etc.

When characterized in terms of the area occupied by the footprint of the depressions, each of the depressions may have a footprint with an area of about 4 square millimeters ($mm^2$) or more. In other situations, each of the depressions may have footprints with an area of about 8 $mm^2$ or more.

Another manner in which the depressions may be characterized is in terms of the largest footprint dimension as measured on the surface of the transfer roll. When characterized in terms of the largest footprint dimension of the footprint, it may be that the depressions have a largest footprint dimension of about 2 mm or more, in some instances about 5 mm or more.

Yet another manner in which the depressions used in connection with the present invention may be characterized is in terms of depression volume. For example, the depressions may have a depression volume of at least about three (3) cubic millimeters ($mm^3$) or more, or alternatively a depression volume of about five (5) cubic millimeters or more. Volume may be important because at least some of the molten thermoplastic composition may be retained within the depression during the transfer process, i.e., the depression volume may preferably be oversized relative to the preferred volume of the discrete polymeric regions to be formed by the depressions to compensate for retention of thermoplastic composition within the depressions.

The orientation of the depression on a transfer roll may be selected based on a variety of factors. The elongated depression may be aligned in the machine direction (i.e., the direction of travel of a substrate), in the cross-web direction (i.e., transverse to the direction of travel of the substrate), or any other orientation between machine direction and cross-web direction.

Attachment of two substrates 105, 106 as shown in FIG. 20 may be accomplished using the deposited polymeric regions of the tab substrate alone when the lamination is performed, while the polymer regions are still in a somewhat molten state such that they can bond with counterpart polymeric regions on the opposing substrate or to the opposing substrate itself. One advantage of this construction is that the lamination may be accomplished without the need for additional materials and/or process steps. The lamination between substrates may alternatively be assisted by a variety of materials and/or techniques known to those skilled in the art, e.g., thermal bonding, adhesives, resins, tie films/webs, etc. See, e.g., U.S. Pat. Nos. 2,787,244; 3,694,867; 4,906,492; 5,685,758; and 6,093,665.

The process of providing tab substrates includes delivering a supply of a molten thermoplastic composition to the exterior surface of one or both of transfer rolls 101 or 102 which include a one or more depressions formed in its exterior surface forming the tab substrate. The molten thermoplastic composition is supplied to the exterior surface of the transfer roll by a delivery apparatus in the form of a trough 111 and/or 112 (or other supply apparatus, e.g., extruder, gear pump, etc.).

The excess molten thermoplastic composition is wiped or removed from the exterior surface by a doctor blade acting against the exterior surface of the transfer roll. Although it may be ideal to remove all of the thermoplastic composition from the exterior surface of the transfer roll, some of the thermoplastic composition may remain on the exterior surface after wiping by the doctor blade.

The depressions formed in the exterior surface of the transfer rolls 101 or 102 preferably receive a portion of the molten thermoplastic composition when the molten thermoplastic composition is deposited on the exterior surface of the transfer roll. If the depressions are not completely filled during or by the deposition of molten thermoplastic composition, the wiping action of the doctor blade on the exterior surface of the transfer roll may assist in substantially filling the depressions with molten thermoplastic composition.

With the depressions at least partially filled with the desired molten thermoplastic composition, the transfer roll continues to rotate until the depressions and the molten thermoplastic composition they contain are forced into contact with the substrate against backup roll 103 or 104 at the transfer nip 113 or 114 (i.e., the nip formed by the transfer roll and the backup roll). It is at this point that transfer of the molten thermoplastic composition in the depressions to the substrate begins. It should be understood that under certain conditions, only a portion of the thermoplastic composition in the depressions might transfer to the substrate.

When a substrate that includes one or more porous major surfaces on which the molten thermoplastic composition is deposited is used a mechanical bond is preferably formed by infiltration of the molten thermoplastic composition into the porous surface of the substrate. The term "porous" includes both structures that include voids formed therein, as well as structures formed of a collection of fibers (e.g., woven, nonwoven or knit) that allow for the penetration of molten thermoplastic compositions.

The nip pressure between the transfer roll and the backup roll is preferably sufficient such that a portion of the thermoplastic composition infiltrates and/or encapsulates a portion of the porous substrate to improve attachment of the tab substrate polymer to the substrate(s). Where the surface of the substrate includes fibers (e.g., where the substrate includes woven, nonwoven, or knit materials on its major surfaces), it may be preferred that the thermoplastic composition encapsulate all or a portion of at least some of the fibers on the surface of the substrate to improve attachment of the discrete polymeric regions to the substrate.

Under some conditions the molten thermoplastic composition in the depressions may completely permeate the substrate if, e.g., the substrate is porous throughout its thickness. In other instances, penetration of the molten thermoplastic composition may be limited to the outer layer or layers of the substrate.

It should, however, be understood that although the outer surfaces of the substrate may exhibit some porosity, that porosity may not necessarily extend through the entire thickness of the substrate. For example, the substrate may have a variety of different layers, with one of the layers being substantially non-porous. In another alternative, the overall thickness of the substrate may render it non-porous as a whole, even though the outer surfaces of the substrate exhibit some porosity as discussed above.

The backup roll 103 or 104 may possess a variety of different characteristics depending on the types of substrate materials and/or molten thermoplastic compositions being processed. In some instances, the exterior of the backup roll may be a rubber or other conformable material that conforms to the shape of the transfer roll. If a conformable material such as rubber is used, it may, e.g., have a durometer of, e.g., about 10–90 Shore A.

The substrate 106 and/or 105 then continues around the backup roll. In some instances, a portion of the molten thermoplastic composition in the depressions may remain in the depressions while the substrate is pulled away from the transfer roll. As a result, the molten thermoplastic composition in the depressions may tend to elongate or string between the depressions in transfer roll and the substrate.

A device, such as a hot wire may be used to sever any strands of thermoplastic composition that may be formed as the substrate separates from the transfer roll. Other devices and/or techniques may be used to accomplish the desired severing of any molten thermoplastic composition strands. Examples may include, but are not limited to hot air knives, lasers, etc. Furthermore, under certain conditions, stringing of the thermoplastic composition may not be encountered during manufacturing. The formed precursor web 107 is then fed to a die cut station 108 to form a partially cut precursor web 109 which can then be wound into a roll.

Although the substrate can be inherently extensible, a nonextensible substrate can be made extensible by, e.g., providing slits in the substrate. The slits are preferably spanned by at least one of the discrete elastomeric polymeric regions. Some exemplary slitting processes to provide or improve extensibility of a substrate are described in International Publication No. WO 96/10481. Other techniques may also be used to provide or improve the extensibility of substrates used in connection with the present invention. For example, the mechanical stretching processes described in U.S. Pat. Nos. 4,223,059 and 5,167,897 may be used to provide or improve extensibility.

The deposition of elastomeric thermoplastic compositions onto substrate such as to form the elasticized tab portion of FIG. 17 is accomplished in much the same manner as used in connection with the deposition of the tab substrate formed of nonelastomeric thermoplastic compositions.

The system may also laminate substrates together, each using both the elastomeric and nonelastomeric printed discrete polymeric regions for the FIG. 17 embodiment or the like as described above. The FIG. 20 system could be used for the purpose where one transfer station deposits nonelastomeric discrete tab substrates onto a substrate 106 and the second transfer station produces elastomeric discrete polymeric regions on second substrate 105. Both substrates 105 and 106 are then directed into a laminating station 100 that produces a laminated composite web 107 which, in the depicted embodiment, would provide both the nonelastomeric tab element and the elastomeric discrete polymeric regions located within the surrounding layers of substrates as shown in FIG. 17.

As with the nonelastomeric thermoplastic compositions described above, elastomeric thermoplastic compositions used for elastic discrete polymeric regions should be capable of flowing or entering into depressions formed in a polymer transfer roll as will be described below. Suitable elastomeric thermoplastic compositions are those that are melt processable. Such polymers are those that will flow sufficiently to at least partially fill the depressions, yet not significantly degrade during a melt process. A wide variety of elastomeric thermoplastic compositions have suitable melt and flow characteristics for use in the process of the present invention depending on the geometry of the depressions and the processing conditions. It may further be preferred that the melt processable materials and conditions of processing are selected such that any viscoelastic recovery properties of the thermoplastic composition do not cause it to significantly withdraw from the wall(s) of the depressions until transfer of the thermoplastic composition to a substrate is desired.

As used in connection with the present invention, "elastomeric" means that the material will substantially resume its original shape after being stretched. Further, the elastomeric materials may preferably sustain only small permanent set following deformation and relaxation, which set is preferably no greater than about 30 percent and more preferably no greater than about 20 percent of the original length at moderate elongation, e.g., about 50%. The elastomeric materials can be both pure elastomers and blends with an elastomeric phase or content that will still exhibit substantial elastomeric properties at room temperature. U.S. Pat. No. 5,501,679 provides some further discussion regarding elastomeric materials that may be considered for use in connection with the present invention.

The elastomeric thermoplastic compositions can include one or more polymers. For example, the elastomeric thermoplastic composition could be a blend with an elastomeric phase such that the composition exhibits elastomeric properties at room temperature. Suitable elastic thermoplastic polymers include block copolymers such as conventional A-B or A-B-A block copolymers (e.g., styrene-isoprene-styrene, styrene-butadiene-styrene, styrene-ethylene-butylene-styrene block copolymers), elastomeric polyurethanes, olefinic elastomers, particularly elastomeric ethylene copolymers (e.g., ethylene vinyl acetates, ethylene/octene copolymer elastomers, ethylene/propylene/diene terpolymer elastomers), as well as mixtures of these with each other, with other elastomeric thermoplastic polymers, or with nonelastomeric thermoplastic polymers.

The elastomeric thermoplastic compositions used in connection with the present invention can also be combined with various additives for desired effect. These include, for example, fillers, viscosity reducing agents, plasticizers, tackifiers, colorants (e.g., dyes or pigments), antioxidants, antistatic agents, bonding aids, antiblocking agents, slip agents, stabilizers (e.g., thermal and ultraviolet), foaming agents, microspheres, glass bubbles, reinforcing fibers (e.g., microfibers), internal release agents, thermally conductive particles, electrically conductive particles, and the like. The amounts of such materials that can be useful in the thermoplastic compositions can be readily determined by those skilled in the art of processing and using such materials.

In addition to the deposition of nonelastic or elastic thermoplastic polymer in discrete regions, it is also contemplated that additional materials can be coated onto a major surface of the substrate using known methods. Such materials could be, for example adhesives, as described in, e.g., U.S. Pat. Nos. 5,019,071; 5,028,646; and 5,300,057; or cohesives as described in, e.g. U.S. Pat. Nos. 5,389,438 and 6,261,278.

What is claimed is:

1. A fastening tab laminate for use in a slot and tab closure system comprising tab portion having a rigid tab member and a related flexible tab carrier substrate wherein the rigid tab member has a outer edge and an inner edge, the inner edge forming at least one lip portion, the tab member formed by a rigid tab substrate laminated to at least one flexible substrate web which substrate web also forms at least in part the tab substrate carrier which flexible web layer is in a single plane where it is continuous between the tab carrier substrate and the rigid tab member, such that the tab carrier substrate and the rigid tab members are coplanar and wherein the lip portion is detached from the tab carrier substrate such that it can pivot away from the coplanar tab carrier substrate.

2. The fastening tab laminate of claim 1 wherein the at least one substrate web is a porous web.

3. The fastening tab laminate of claim 2 wherein the at least one flexible substrate web is a nonwoven fibrous web.

4. The fastening tab laminate of claim 2 wherein the rigid tab substrate is a thermoplastic polymer material.

5. The fastening tab laminate of claim 4 wherein the rigid tab substrate thermoplastic material is at least partially penetrated into the porous structure of the flexible substrate web.

6. The fastening tab laminate of claim 5 wherein the at least one flexible substrate web is attached to the tab members to extend over at least 25% of the tab member.

7. The fastening tab laminate of claim 6 wherein the flexible substrate web extends over at least 50% of the tab member.

8. The fastening tab laminate of claim 6 wherein the flexible substrate web extends over at least 10% of the tab carrier substrate.

9. The fastening tab laminate of claim 8 wherein the flexible substrate web extends over at least 25% of the tab carrier substrate.

10. The fastening tab laminate of claim 1 wherein the rigid tab substrate is laminated onto two flexible substrate webs on opposite faces of the rigid tab substrate.

11. The fastening tab laminate of claim 10 wherein both flexible substrate webs also form at least in part the tab carrier substrate.

12. The fastening tab laminate of claim 11 wherein at least one elastic element is attached to a flexible substrate web forming the tab carrier substrate so as to provide an elastic fastening tab laminate.

13. The fastening tab laminate of claim 1 wherein the rigid tab member has a curved outer edge.

14. The fastening tab laminate of claim 13 wherein the rigid tab member has an curved inner edge forming the lip portion, which lip portion extends at least 3 to 10 mm from a pivot point or region.

15. The fastening tab laminate of claim 1 wherein the rigid tab member has a Gurley stiffness of from 500 to 8000.

16. The fastening tab laminate of claim 15 wherein the tab carrier substrate has a Gurley stiffness of from 1 to 500.

17. The fastening tab laminate of claim 16 wherein the rigid tab member has a Gurley stiffness at least two times greater than that of the tab carrier substrate.

18. The fastening tab laminate of claim 17 wherein the rigid tab member stiffness is at least five times as great as the tab carrier substrate.

19. The fastening tab laminate of claim 17 wherein the tab substrate is a thermoplastic polymer having a thickness of from 0.1 to 1.0 mm.

20. The fastening tab laminate of claim 19 wherein the tab substrate is a thermoplastic polymer having a thickness of from 0.2 to 0.8 mm.

21. The fastening tab laminate of claim 1 wherein the lip portion pivots away from the tab carrier substrate forming a V-shaped gap which lip portion extends at least 3 mm from a pivot point or region.

22. The fastening tab laminate of claim 1 wherein the lip portion pivots away from the tab carrier substrate forming a V-shaped gap which lip portion extends at least 3 to 10 mm from a pivot point or region.

23. The fastening tab laminate of claim 21 wherein the lip portion is a reverse mirror image of a cutout portion of the tab carrier substrate.

24. The fastening tab laminate of claim 1 wherein the tab member further comprises at least one wing member that extends into that portion of the tab member comprising the lip portion in the lengthwise direction of the tab portion, which wing elements are not pivotable away from the carrier substrate.

25. The fastening tab laminate of claim 24 wherein the at least one wing member is attached to the tab carrier substrate.

26. The fastening tab laminate of claim 25 wherein there are two wing members on the outermost edges of the tab member outside of all lip portions.

* * * * *

UNITED STATES PATENT AND TRADEMARK OFFICE
CERTIFICATE OF CORRECTION

PATENT NO.      : 6,880,211 B2
DATED           : April 19, 2005
INVENTOR(S)     : Jackson, Byron M.

Page 1 of 1

It is certified that error appears in the above-identified patent and that said Letters Patent is hereby corrected as shown below:

Column 16,
Line 39, before "substrate" insert -- flexible --.

Signed and Sealed this

Thirteenth Day of December, 2005

JON W. DUDAS
*Director of the United States Patent and Trademark Office*